United States Patent
Engin

(10) Patent No.: US 9,808,335 B2
(45) Date of Patent: Nov. 7, 2017

(54) ADJUSTABLE ELASTIC ANTAGONIST MUSCLE REPLACEMENT MECHANISM

(71) Applicant: Murat Sinan Engin, Samsun (TR)

(72) Inventor: Murat Sinan Engin, Samsun (TR)

(*) Notice: Subject to any disclaimer, the term of this patent is extended or adjusted under 35 U.S.C. 154(b) by 0 days.

(21) Appl. No.: 14/366,001

(22) PCT Filed: Dec. 21, 2012

(86) PCT No.: PCT/IB2012/057612
§ 371 (c)(1),
(2) Date: Jun. 17, 2014

(87) PCT Pub. No.: WO2013/093879
PCT Pub. Date: Jun. 27, 2013

(65) Prior Publication Data
US 2014/0371854 A1 Dec. 18, 2014

(30) Foreign Application Priority Data
Dec. 21, 2011 (TR) .................................. 2011/12752

(51) Int. Cl.
*A61F 2/08* (2006.01)
(52) U.S. Cl.
CPC ........ *A61F 2/08* (2013.01); *A61F 2002/0894* (2013.01); *A61F 2210/0057* (2013.01); *A61F 2250/0003* (2013.01)
(58) Field of Classification Search
CPC ........................... A61F 2/08; A61F 2002/0894
See application file for complete search history.

(56) References Cited

U.S. PATENT DOCUMENTS

| | | | |
|---|---|---|---|
| 3,882,551 A * | 5/1975 | Helmer | ..................... A61F 2/08 128/DIG. 21 |
| 5,185,932 A * | 2/1993 | Caines | ........................... 30/288 |
| 6,168,634 B1 | 1/2001 | Schmitz | |
| 2002/0026794 A1* | 3/2002 | Shahinpoor et al. | ........... 60/508 |
| 2014/0031952 A1* | 1/2014 | Harshbarger | ............. A61F 2/72 623/25 |

FOREIGN PATENT DOCUMENTS

| | | |
|---|---|---|
| DE | 19830559 C1 | 1/2000 |
| DE | 20216749 U1 | 7/2003 |
| GB | 2244006 A | 11/1991 |
| WO | WO03067097 A1 | 8/2003 |

* cited by examiner

*Primary Examiner* — Brian Pellegrino
(74) *Attorney, Agent, or Firm* — Gokalp Bayramoglu

(57) ABSTRACT

The present invention is an anatomic system which uses the principle of applying higher elastic tonus than the rest tonus of the agonist muscles to provide the function of the antagonist muscles, and which is designed in a simplest way to provide the said purpose and which can be integrated to the body. The static mechanism of the invention is an elastic mechanism which applies a continuous stable tension in order to keep the joints open. The tension of the mechanism is calibrated by increasing or decreasing the amount of the liquid in a chamber which has flexible and elastic walls up to a certain via a port. In the dynamic mechanism of the invention, the tension applied by the elastic mechanism can be changed according to the motion the patient wants to perform.

8 Claims, 5 Drawing Sheets

ADJUSTABLE ELASTIC ANTAGONIST MUSCLE REPLACEMENT MECHANISM

FIELD OF THE INVENTION

Skeletal muscles provide the mobility of the joints in human body. Especially in the extremities, the movement is provided by "Agonist-antagonist muscle pairs". Within this concept, for example the flexion of the wrist is provided by the agonist musculus flexor carpi radialis duo, and musculus flexor carpi ulnaris, whereas extension of the same joint is provided by antagonist muscles musculus extensor carpi radialis and ulnaris. The stronger ones of the said muscle pairs are the agonist muscles and those are the ones which generally function against the external load. The usual duty of the antagonist muscles is to bring the extremity to the position in which it will function. When the antagonist muscle functions are extensively lost (especially in irrecoverable nerve lesions), even if the agonist muscles are functional, the limb cannot function and malformation is seen in the limb. The invention relates to biocompatible elastic units and the integration systems of the said units to living organism which aim to replace the functions of the antagonist muscles, which are weaker than the agonist muscles, by applying stable or variable tension.

BACKGROUND OF THE INVENTION

The surgical methods that can be applied for replacement of lost muscle functions can also be applied in antagonist muscle function losses. Tendon and muscle transfers are among the said implementations. By this means, a musculotendinous unit in voluntary control of the patient substitutes for the lost function of the muscle. Also, there are some techniques specific to antagonist muscle losses. The said techniques exploit the fact that the antagonist tonus is weaker than the agonist tonus. In order to eliminate the deficiency of an agonist muscle, actuator type motors, which can provide linear movement with high power, are needed and the studies to accomplish this feat are in progress. However, in order to eliminate the deficiency of the antagonist muscles, the mechanism which can implement higher tension than the resting tonus of agonist muscles that is the tension which they apply when the muscles do not generate any function will be adequate. The said mechanisms keep the joints at a position where they can generate function with stable tension which they implement during rest, and a person can overpower the said tension with the strength of the agonist muscles when he/she wants to generate a function. Depending on the said principle, splints and orthesis were produced which provide the function of the antagonist muscles in the affected limb with the elastic systems externally. For example, in a nervus radialis lesion which results in the paralysis of hand extensors, there are splints with springs which bring the wrist and the fingers to extension. The said splints keep the hand open such that it will grab an object and when the patient grabs an object, he/she overpowers the strength of the springs with the tension of agonist muscles and can perform the grabbing. Similarly, there are systems with spring which pull the foot upwards from its metatarsus in order to eliminate foot drop seen as a result of nervus peronealis injury, and enable the patient to pull the tip of her/his foot upwards during stepping.

Tendon and muscle transfers are technically challenging operations which require sacrificing the function of another muscle, and can prove taxing for the patient.

The splints and the orthesis which will open the joints externally appear unpleasant, their use is difficult and the functional improvements they provide are limited. Furthermore, the said systems function with a stable tension without any interaction with the neuromotor activity of the patient, and they cannot provide a decrease or increase in their tensions such that they will adapt muscle activity intensity at a certain moment.

In addition to the said methods used practically in humans, there are several patent documents in the technique related with the object of the invention.

FR 2810877: Joint ligament implant prosthesis having elasticity and which can be fastened to the bone from both ends. However the said invention does not have a mechanism providing adjustable tension as well as it is not designed to replace a muscle function.

US 2009048479: Urethra strip manufactured from prolene mesh, developed for incontinence. Mesh pattern is also used in the project which is introduced, the structure of the mesh is commonly used and the product does not have the adjustable elastic structure of the design presented in the project which is introduced.

US 2010030332, WO 2005020857: An intraocular lens model the accommodation of which can change with the contact of ciliary muscle. By means of a reservoir which can inject liquid into the said product, it can fit to the ciliary muscle and its diopter can be adjusted to a certain level, however the field of usage and operating principle is completely different from the project which is introduced.

WO2011054394 (A1): This patent is an actuator model comprised of a plurality of cells which will respond to electric current, and providing linear movement via the electro active materials inside the cells.

1—The design does not mention the use of electrorheological fluid.

2—It does not include details of how it will be used in an organism and how it will be integrated.

3—It does not describe concretely how it will be controlled by the individual.

CN201404216: The invention disclosed in the patent aims to amplify the myoelectric activity in the limbs and stimulate the paralyzed muscles directly. The technology in the said invention is already used in myoelectric prosthesis (electronic hand prosthesis).

DESCRIPTION OF THE PARTS IN THE FIGURES

Figure 1:
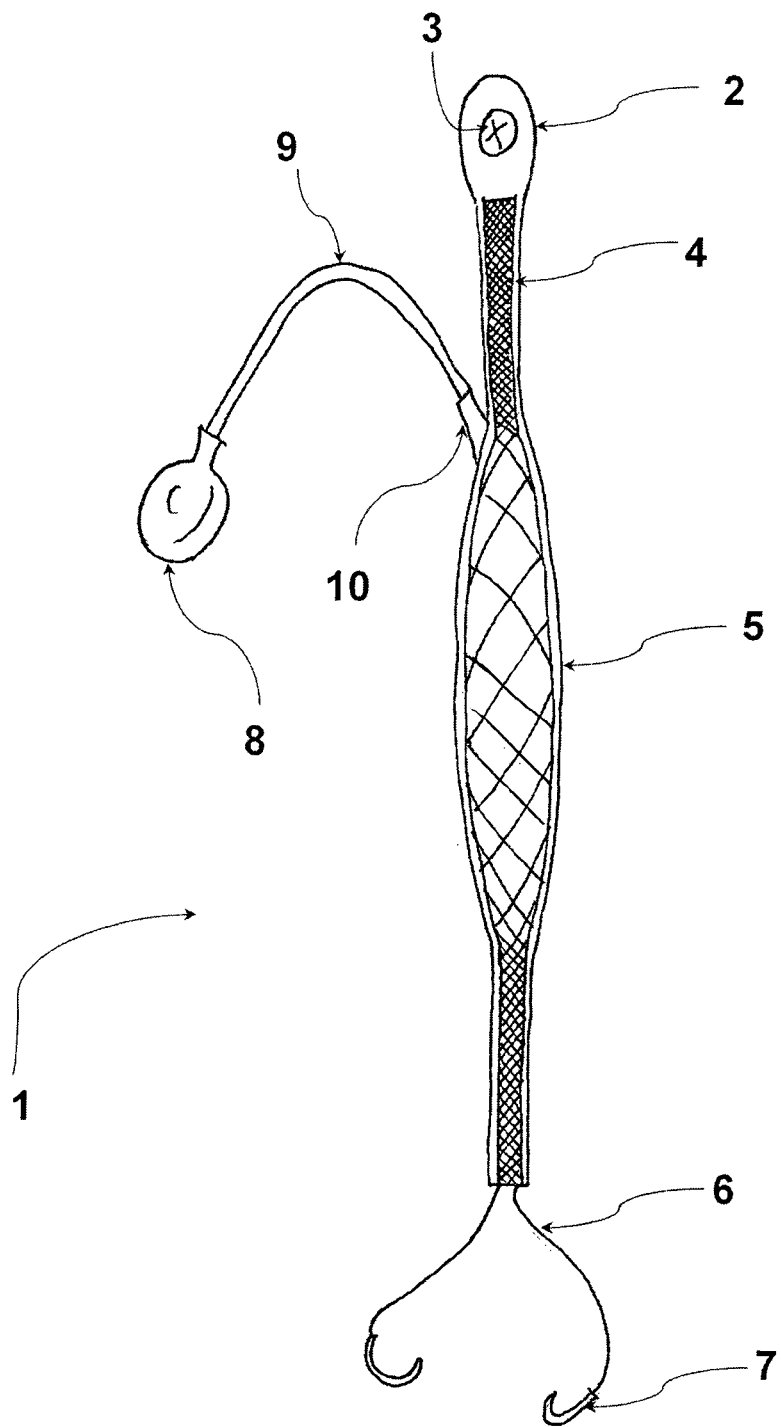
FIG. 1 is the scheme of an adjustable elastic antagonist muscle replacement mechanism (in a static structure)
Figure 2:
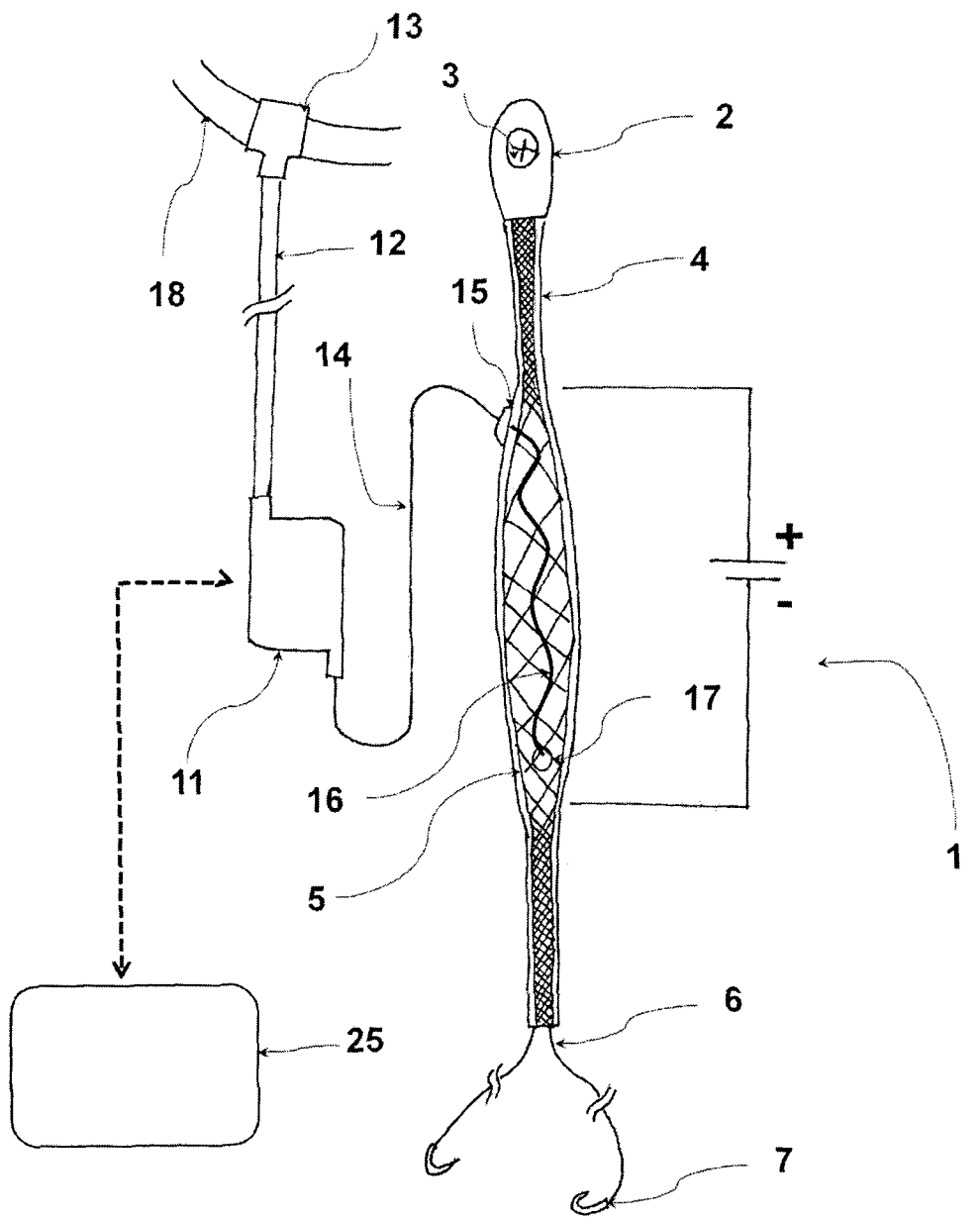
FIG. 2 is the scheme of an adjustable elastic antagonist muscle replacement mechanism (in a dynamic structure)

1. Adjustable elastic antagonist muscle replacement mechanism
2. Screw hole
3. Screw 4. Biocompatible elastomer coated close polymer mesh
5. Elastic tension chamber
6. Polymer suture
7. Suture needle
8. Injection port
9. Connection tube
10. Nozzle
11. Sensor-stimulator unit
12. Afferent cable
13. Sensor electrode
14. Efferent cable
15. Stimulator electrode
16. Stimulator electrode, anode cable
17. Stimulator electrode, anode end and inlet
18. Peripheral nerve
19. epicondylus lateralis humeri
20. musculus extensor carpi radialis longus tendon
21. Triple dynamic tension module
22. Double dynamic tension module
23. nervus radialis
24. nervus medianus
25. External calibration unit

DETAILED DESCRIPTION OF THE INVENTION

Figure 3:
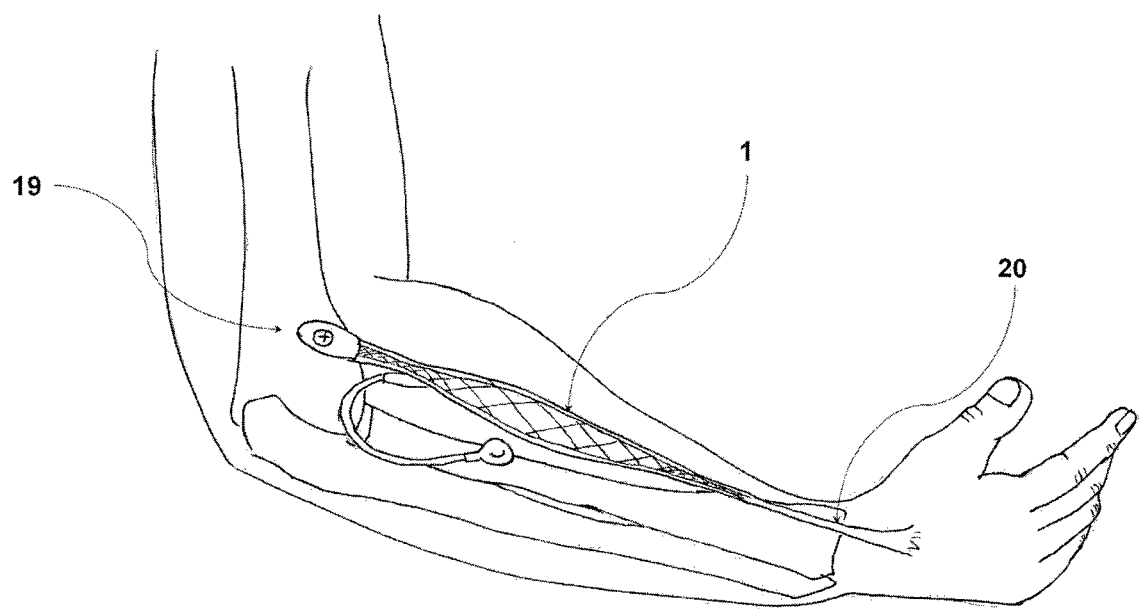
FIG. 3 is the schematic view of the embodiment of an adjustable elastic antagonist muscle replacement mechanism in a static structure.

The Static Embodiment of the Adjustable Elastic Antagonist Muscle Replacement Mechanism The static system is essentially an implant (1) produced from biocompatible materials which applies the tension to be applied by the muscle or muscle groups which have lost their function via an adjustable elastic system. The implant system is formed in a length and thickness according to the anatomic region to which it will be placed and the length and strength of the muscle which it will replace. In cases wherein a plurality of muscles which are close to each other anatomically will be replaced, the implants can be combined in a required number. The inner material of the implant is a close mesh manufactured from a biocompatible polymer (for example PEEK-CFr), its outer surface is coated with a biocompatible elastomer (for example Medical silicon) (4). The polymer mesh becomes loose in the middle part of the implant, and the silicon elastomer expands such that it will form a chamber (5) shaped like shuttle. The said part, which has a limited elasticity in its wall, is the elastic tension chamber of the mechanism and the tension strength it has can be changed with the amount of the fluid in its chamber (for example 0.9% isotonic NaCl). With this purpose, an injection port (8) is connected to a nozzle (10) reinforced with a hardened elastomer clamp in the least mobile proximal part of the chamber via biocompatible elastomer tube (9), and liquid in a desired amount can be filled into the chamber via an injector from the said port placed subcutaneously or the liquid inside the chamber can be discharged. The function of the implant is to apply a static tension between two points. The said two points can be bone or soft tissue (tendon, ligament etc.) depending on the situation. The end of the mechanism to be attached to the bone is a screw hole (2) comprised of pressed polymer mesh between two biocompatible polymer layer and the mechanism can be screwed to the bone from this point. At the end of the mechanism to be attached to the soft tissue or tendon, the polymer mesh ends with two polymer sutures (6) which have needle (7) in desired features. According to the condition of the anatomic region which will be reconstructed, an implant can be produced such that it will attached to the bone from both ends, to the soft tissue from both ends, or to the bone from one end, to the soft tissue from the other end. The one shown in FIG. 1 is the version which is produced such that it will be attached to the bone from its proximal end, to the tendon from its distal end. The system (1) replacing musculus extensor carpi radialis longus muscle with demonstrative purpose is seen in FIG. 3. While the system is screwed to the epicondylus lateralis humeri (19) from its proximal end via the screw hole, it is sutured to the extensor carpi radialis longus tendon from its distal end via the sutures (20). The system is attached such that it will keep the joints, which the muscle that will be replaced, in natural position with the chamber 30% full, and the port is left at a pouch formed under the skin. The tension provided by the system can be increased or decreased during the physiotherapy after the operation if it is necessary. After that point, the system will hold the joints of the patient open at rest. When the patient wants to produce work (like grabbing an object), he/she will perform the movement by overpowering the tension of the elastic system with the tonus of the agonist muscles. Similarly, the system can also be used in antagonist deficiencies of the lower extremity.

Figure 4A:
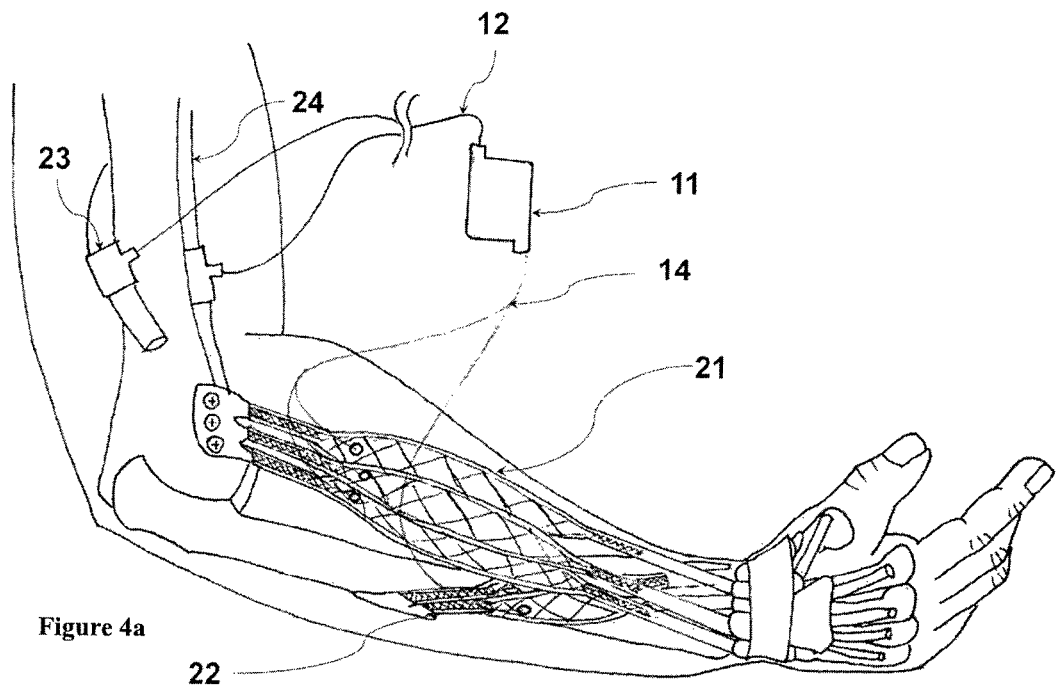
FIG. 4 is the schematic view of the embodiment of an adjustable elastic antagonist muscle replacement mechanism in a dynamic structure.
Figure 4B:
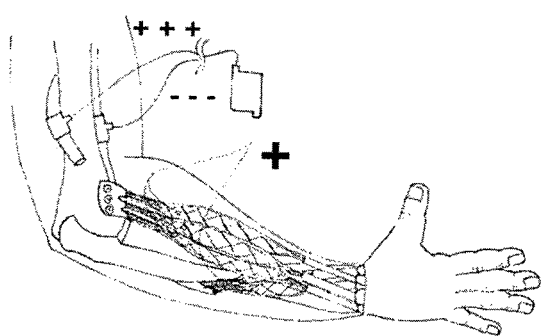
Figure 4C:
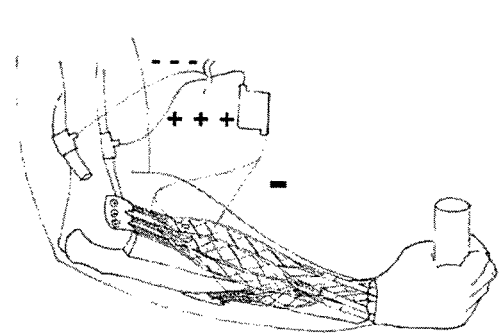
Figure 5:
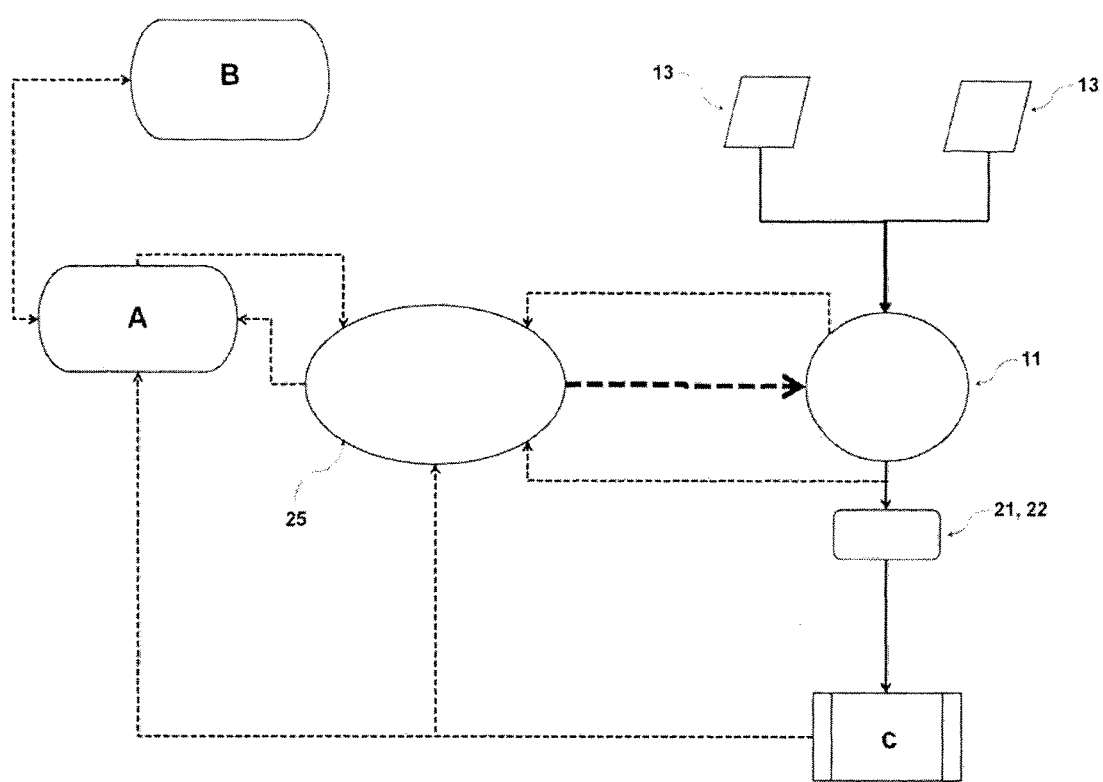
FIG. 5 is the flowchart of the sensor-stimulator system calibration and operation.

The Dynamic Embodiment of the Adjustable Elastic Antagonist Muscle Replacement Mechanism The system is essentially an implant manufactured from biocompatible materials, which applies the tension, which the muscle or muscle groups that have lost their function will apply, via an elastic system the power of which can change under the control of an electronic system which detects the muscle activity the patient wants to perform. The implant is formed in a length and thickness according to the anatomic region to which it will be placed and the length and strength of the muscle which it will replace as in the static implementation. In cases wherein a plurality of muscles which are close to each other anatomically will be replaced, the implants can be combined in a required number. The inner material of the implant is a close mesh manufactured from a biocompatible polymer (for example PEEK-CFr), its outer surface is coated with a biocompatible elastomer (for example Medical silicon) (4). Similarly, it can be attached to the compatible anatomic structures from its both ends via a screw hole (2) and screw (3) and/or tendon suture (6) and the needle (7). The difference of the dynamic system from the static system is the content of the elastic tension chamber (5). In the tension chamber similar to the one in the static system, electrorheologic fluid in a stable amount is present. The electrorheologic fluids are the liquids the viscosity of which change when they are subjected to electric current, and the electric current to be applied to the tension chamber is controlled by a sensor-stimulator unit (11) which detects the electric activity generated by the peripheral nerves (18) of the patient via sensor electrode (13) and an afferent cable system (12). The unit transfers the electric current to the stimulator electrode (15) at the proximal end of the chamber via an efferent cable (14). The cathode end of the electrode passes the wall of the elastic unit and contacts the fluid, and the insulated anode cable (16) goes until the distal end of the chamber in a curved way and reaches the content of the chamber passing through the inlet (17) supported by the elastomer disc reinforced in that region. In FIG. 4a, the embodiment of the system is shown such that it will replace all basic forearm extensors. Triple module shown as number 21 is screwed to the bone at proximal and fixed on the tendon at distal such that it will replace the extensor carpi radialis, extensor digitorum communis and extensor carpi ulnaris muscles, and the double module shown as number 22 is screwed to the bone at proximal and fixed on the tendon at distal such that it will replace the abductor pollicis longus ve extensor pollicis longus muscles. The sensor electrodes (13) of the microprocessor unit can be connected to the proximal end of the antagonist radial nerve (23) which is injured or to the agonist median nerve (24) which is intact or both, according to the surgical anatomy. Stimulator electrodes (15) are connected to the related tension units. The attachment is performed in a tension such that it will keep the hand joints at a natural position when the system is in 30% tension potential, and the sensor-stimulator unit (11) is left in a pouch formed under the skin. During physiotherapy after the operation, sensor-stimulator unit is calibrated such that it will provide tension compatible with the desired movement (FIG. 5). For this, a wireless connection is formed between the sensor-stimulator unit (11) implanted to the patient (B) and the external calibration terminal (25) which is controlled by the healthcare professional (A) who follows the patient. As the patient exerts to perform a certain voluntary movement, the reflection of this effort on the sensor electrode(s) (13) is digitalized by the unit and sent to the external calibration terminal (25). When the data processed by the operator who is in continuous communication with the patient is gathered such that it can be described as a distinct stimulus pattern, it can be attributed to a certain motion pattern. At this point, the calibration data (thick interrupted line) are loaded to the sensor-stimulator unit, and the unit sends the stimulus which will provide the desired tension to the tension units (21, 22) when it picks up the given stimulus pattern. As a result, a motion (C) is generated. Under the supervision of the operator, calibration and error control feedbacks received from the patient, sensor-stimulator unit and the motion that is generated are processed and after it is confirmed that they transform into an antagonist tonus that will conform the desired motion pattern of the voluntary effort, the calibration data takes its final form and the connection between the sensor-stimulator unit and the external calibration terminal is ended. After this point, the sensor-stimulator unit can adjust the tension of the mechanism when the sensor receives a stimulant pattern which it can identify from the electrodes independent from the external calibration terminal. In a manner of speaking, in the example of FIG. 4a, both the median and the radial nerve to which the sensor electrodes are connected reflect resting potential, and the system applies antagonist tension such that it will keep the hand in neutral position. In FIG. 4b, upon the patient wants to perform extension, inhibition potentials will be reflected on the median nerve innerving the agonist muscles, and the excitation potentials will be reflected on the stump of the radial nerve innerving the antagonist muscles. The sensor-stimulator unit calibrated appropriately will identify the said changes and increase the viscosity of the electrorheologic fluid in the chamber of the unit and thus the antagonist tension power. Similarly, when the patient—in a manner of speaking—wants to grab an object, this time the unit will decrease the viscosity of the fluid, thus the antagonist tension power as a respond to the excitation in the agonist nerve and/or the inhibition at the antagonist nerve stump (FIG. 4c). The said system can transform the electrophysiological activity in the healthy nerves into a stimulant by shifting the function of the injured nerves to the healthy nerves. From this aspect, not only in this invention, it can also be used for the signal regulation of all kind of actuator or stimulators used in denerved but healthy muscles. The system can be calibrated such that it will make each unit to apply different antagonist tonus in subtler, more delicate movements. Similarly, the said system can also be used in antagonist failures of the lower extremity.

The invention claimed is:
1. An adjustable elastic antagonist muscle replacement mechanism, which detects the muscle activity the patient wants to perform, capable of being changed under the control of an electronic system, of an elastic system which provides the tension applied by muscle or muscle group which lost their function, the mechanism comprising:
  an adjustable tension chamber, which is formed from a loose polymer mesh in its middle segment, wherein the loose polymer mesh comprises a shuttle structure, and wherein the outer surface of the loose polymer mesh is coated with biocompatible elastomer; wherein the adjustable tension chamber contains an electrorheological fluid in it;
  a screw hole is placed on one end of the adjustable elastic antagonist muscle replacement mechanism and is configured for attaching the adjustable tension chamber to the bones;
  a tendon suture is placed on the other end of the adjustable elastic antagonist muscle replacement mechanism and is configured for attaching the adjustable tension chamber to the tendons or soft tissues;
  a sensor-stimulator unit is adapted to configure the tension that is applied by the adjustable tension chamber and is adapted to change viscosity of the electrorheological fluid in the adjustable tension chamber;
  a sensor electrode for detecting the electric activity generated by the peripheral nerves of the patient;
  an afferent cable for transferring detected electric activity to the sensor-stimulator unit; wherein the sensor-stimulator unit is capable of generating an electric current according to the detected electric activity;
  an efferent cable for transferring the electric current to a stimulator electrode connected to the adjustable tension chamber;
  wherein the adjustable tension chamber is capable of applying a variable tension between two anatomic localization.

2. The adjustable elastic antagonist muscle replacement mechanism according to claim 1, wherein the stimulator electrode is connected to a proximal part of the adjustable tension chamber; a cathode end of the stimulator electrode enters in the proximal part of the adjustable tension chamber and contacts the electrorheological fluid, and an anode cable of the stimulator electrode extends from the proximal part in a curved way towards a distal part of the adjustable chamber and enters into the adjustable tension chamber from the distal part and contacts the electrorheological fluid therein.

3. The adjustable elastic antagonist muscle replacement mechanism according to claim 1, wherein the sensor-stimulator unit is adapted to digitalize the reflection of the effort on the sensor electrode(s) and send to an external calibration terminal as the patient exerts to perform a certain voluntary movement.

4. The adjustable elastic antagonist muscle replacement mechanism according to claim 1, wherein a sensor-stimulator unit is adapted to calibrate to provide tension compatible with the desired movement during physiotherapy after the operation.

5. An adjustable elastic antagonist muscle replacement mechanism, which detects the muscle activity the patient wants to perform, capable of being changed under the control of an electronic system, of an elastic system which provides the tension applied by muscle or muscle group which lost their function, the mechanism comprising:
  a plurality of adjustable tension chambers, that are formed from a loose polymer mesh in their middle segments, wherein the loose polymer mesh comprises a shuttle structure, and wherein the outer surfaces of the loose polymer mesh are coated with biocompatible elastomer; wherein the plurality of adjustable tension chambers contain corresponding electrorheological fluid in them;

a screw hole is placed on one end of the adjustable elastic antagonist muscle replacement mechanism and is configured for attaching the adjustable tension chamber to the bones;

a tendon suture is placed on the other end of the adjustable elastic antagonist muscle replacement mechanism and is configured for attaching the adjustable tension chamber to the tendons or soft tissues;

a plurality of sensor-stimulator units, adapted to configure the tensions that are applied by the adjustable tension chambers and adapted to change viscosity of the electrorheological fluid in the adjustable tension chambers;

a plurality of sensor electrodes configured to detect the electric activity generated by the peripheral nerves of the patient;

a plurality of afferent cable for transferring detected electric activity to the plurality of sensor-stimulator units; wherein the plurality of sensor-stimulator units are capable of generating electric currents according to detected electric activity;

a plurality of efferent cable for transferring the electric currents to a stimulator electrode connected to the plurality of adjustable tension chambers;

wherein the plurality of adjustable tension chambers are capable of applying variable tensions between two anatomic localizations.

6. The adjustable elastic antagonist muscle replacement mechanism according to claim 5, wherein the plurality of stimulator electrodes are connected to a proximal part of the plurality of adjustable tension chambers, each adjustable chamber having a cathode end of the plurality of the stimulator electrodes located in the proximal part of each adjustable tension chamber and contacts the electrorheological fluid, and each adjustable chamber having an anode cable of the plurality of the stimulator electrodes, which extends from the proximal part in a curved way towards a distal part of the adjustable chamber and enters into the adjustable tension chamber from the distal part and contacts the electrorheological fluid therein.

7. The adjustable elastic antagonist muscle replacement mechanism according to claim 5, wherein the plurality of sensor-stimulator units are adapted to digitalize the reflection of the effort on the plurality of sensor electrodes and send to an external calibration terminal as the patient exerts to perform a certain voluntary movement.

8. The adjustable elastic antagonist muscle replacement mechanism according to claim 5, wherein the plurality of sensor-stimulator units are adapted to calibrate to provide tension compatible with the desired movement during physiotherapy after the operation.

* * * * *